United States Patent [19]

Sato et al.

[11] Patent Number: 5,565,409
[45] Date of Patent: Oct. 15, 1996

[54] LIQUID CONCENTRATED HERBICIDAL MICROEMULSION COMPOSITIONS COMPRISING GLYPHOSATE AND EITHER OXYFLUORFEN OR ACIFLUORFEN

[75] Inventors: Tatsuo Sato, Tokyo, Japan; Shuaib A. Khan, Brussels; Robert W. Mitchell, Overijse, both of Belgium

[73] Assignee: Monsanto Company, St. Louis, Mo.

[21] Appl. No.: 218,778

[22] Filed: Mar. 28, 1994

[30] Foreign Application Priority Data

Apr. 2, 1993 [EP] European Pat. Off. .............. 93870063

[51] Int. Cl.$^6$ .......................... A01N 25/30; A01N 57/04; A01N 33/22
[52] U.S. Cl. ........................................ 504/127; 71/DIG. 1
[58] Field of Search ................................ 504/127

[56] References Cited

U.S. PATENT DOCUMENTS

| | | | |
|---|---|---|---|
| 4,399,287 | 8/1983 | Baillie et al. | 548/119 |
| 4,626,274 | 12/1986 | Hausmann et al. | 71/93 |
| 4,994,101 | 2/1991 | Young | 71/83 |
| 5,125,953 | 6/1992 | Gattner et al. | 71/DIG. 1 |

FOREIGN PATENT DOCUMENTS

| | | |
|---|---|---|
| 0143547 | 6/1985 | European Pat. Off. . |
| 2230955 | 11/1990 | United Kingdom . |

OTHER PUBLICATIONS

Wyrill, J. B., et al "Glyphosate Toxicity . . . as Influenced by Surfactants" 0 Weed Science 25 (3):275–287 1977.

*Primary Examiner*—S. Mark Clardy

[57] ABSTRACT

There is disclosed a liquid concentrate herbicidal composition comprising:
  at least 15% by weight based on the total composition of N-phosphonomethylglycine or of a salt thereof or of a mixture of salts thereof (calculated as acid equivalent);
  a water-insoluble diphenyl ether type herbicide (oxyfluorfen or acifluorfen) in the ratio by weight of N-phosphonomethylglycine a.e. to diphenyl ether type herbicide of from about 10:1 to about 100:1;
  about 5 to about 25% by weight of a surface active component comprising a mixture of an alkoxylated fatty amine with a surfactant chemically different from the alkoxylated fatty amine;
  0 to about 10% by weight of solvent, the surface active component optionally with admixture of the solvent being capable of dissolving the diphenyl ether herbicide;
  about 1 to about 25% by weight of a compatibility agent; and
  water if necessary to total 100%.

11 Claims, No Drawings

LIQUID CONCENTRATED HERBICIDAL MICROEMULSION COMPOSITIONS COMPRISING GLYPHOSATE AND EITHER OXYFLUORFEN OR ACIFLUORFEN

The present invention provides concentrated liquid herbicidal compositions comprising glyphosate herbicide and at least one co-herbicide other than glyphosate, which is essentially insoluble in water, more particularly a diphenyl ether type of herbicide.

Glyphosate (N-phosphonomethylglycine) is a widely used non-selective, highly effective herbicide. Glyphosate herbicide is normally provided as a water soluble salt, preferably the isopropylamine (IPA) salt of glyphosate. Liquid concentrated formulations intended to be diluted in a spray tank by the end-user generally contain, in addition to the glyphosate salt, a surfactant or a surfactant mixture which increases the biological effect of the glyphosate herbicide.

Numerous studies have been made on the effect of surfactants on the herbicidal action of glyphosate. Wyrill and Burnside, Weed Science, Vol. 25 (1977), 275–287, for instance reported studies of the effects of many different surfactants including examples from different classes of surfactant. Some classes of surfactant were more effective than others in enhancing the herbicidal effect of glyphosate (used as a solution of the isopropylamine salt). Wyrill and Burnside concluded that an effective surfactant is an important component of any glyphosate spray formulation. The authors also mention that "effectiveness of surfactant combinations is quite variable and difficult to predict—therefore, the indiscriminate addition of surfactants or wetting agents to glyphosate sprays which already contain a surfactant should be avoided".

Glyphosate herbicide is known to act rapidly and effectively but to show visual symptoms at a relatively late stage. It has already been suggested in the art to apply glyphosate herbicide in combination with diphenyl ether type herbicides essentially in order to accelerate the appearance of visual symptoms.

PCT Patent Application WO 84/03607 discloses a herbicidal composition comprising a glyphosate type herbicide and acifluorfen, a diphenyl ether type herbicide. Page 3 thereof contains a broad statement that small amounts of acifluorfen, or its salts, added to glyphosate substantially enhance the speed of phytotoxicity.

Similarly, European Patent Application 0 143 547 discloses a herbicidal composition containing glyphosate and oxyfluorfen, another diphenyl ether type herbicide.

European Patent Application 0 340 583 relates to herbicidal compositions comprising a glyphosate type herbicide (N-(phosphonomethylglycil)sulfonylamine) and a herbicide selected from a group containing inter alia phenoxybenzoic type herbicides.

PCT Patent Application WO 89/03641 discloses a herbicidal composition comprising at least one glyphosate type herbicide and a phenoxybenzoic-type herbicide, the weight ratio of phenoxybenzoic-type herbicide to glyphosate type herbicide being between 1:12 and 1:80.

However, none of the above prior art references discloses or suggests a liquid, concentrated, stable formulated composition comprising glyphosate herbicide and a diphenyl ether type of herbicide.

More recently, European Patent Application 0 448 538 and European Patent Application 0 394 211, in Example 12 thereof, disclose a process for the preparation of a solid formulation comprising N-phosphonomethylglycine or a water-soluble salt thereof and oxyfluorfen. According to EP 0 448 538 a liquid premix comprising oxyfluorfen, at least one surfactant, and water or solvents is prepared at a temperature of from 50° C. to 80° C., thus dissolving oxyfluorfen, and a second premix comprising N-phosphonomethylglycine or a water soluble salt thereof, an acid acceptor if appropriate and preground ammonium sulfate is formed, and both premixes are combined to form an extrudable composition, which is extruded and optionally dried.

Different types of liquid formulated combinations of glyphosate herbicide and co-herbicide have been suggested in the art.

European Patent Application 0 244 754 discloses reportedly stable emulsions of aqueous herbicidal solutions (e.g. of a glyphosate salt) with organic solutions of active material and selected surfactant mixes. The examples disclose emulsions of glyphosate herbicide with metolachlor and glyphosate herbicide with linuron. In the examples, the loading of active material, such as glyphosate, is rather low (3.3 and 5.0 % w/w respectively) in the formulated product. Emulsions, moreover, are known to tend to cream and break, and a formulation that has undergone these processes may give poor results when actually sprayed on plants. Further, emulsions are generally opaque or milky and thus do not always constitute a desirable formulated commercial product; such a product often requires shaking before using.

British Patent Application GB 2 103 487 discloses a water dispersible emulsion composition which contains as the active ingredient a water-soluble herbicide, e.g. the isopropylamine (IPA) salt of glyphosate, combined with a water-insoluble 2-haloacetanilide herbicide, e.g. alachlor. The composition disclosed contains less than 35% w/w of a 62% solution of IPA salt of glyphosate (approximately 16% glyphosate acid equivalent) and the solvent content and the emulsion type formulation are not always considered optimum from a commercial point of view.

Japanese Patent Application 1 203 302 discloses an agricultural ready-to-use composition comprising 0.5–10% by weight of water-insoluble organic solvent of specific gravity less than one, 0.1–1% by weight of a nonionic surfactant of HLB 10 or less, said surfactant optionally containing 30% or less by weight of oil-soluble anionic surfactant, 0.01–1% by weight of a powdery or oily agricultural chemical, and at least 90% by weight of water. The composition is used as it is by forming a suspension without addition of water. The content of agricultural chemical in the formulation is rather low.

PCT Patent Application WO 90/07277 discloses a herbicidal emulsion composition comprising a herbicidally effective amount of an oxadiazolone herbicide, an aromatic solvent in an amount sufficient to dissolve the oxadiazolone herbicide, a herbicidally effective amount of N-phosphonomethylglycine, water in an amount sufficient to dissolve the N-phosphonomethylglycine, an emulsifying agent in an amount sufficient to render the emulsion stable, and optionally a polymeric thickening agent in an amount sufficient to thicken the composition such that at 25° C. the time elapsed for 100 ml of the composition to pass through a measurement orifice of a Ford B2 Cup is in the range of about 20–125 seconds. The content of glyphosate herbicide is rather low and the formulation disclosed requires a relatively large amount of organic solvent, said to be preferably between 30 and 70 percent by weight of the composition.

European Patent Application 0 243 872 discloses pesticidal concentrate compositions comprising 1–55% by weight of a pesticidal component, e.g. glyphosate, in a finely ground and wholly or partially salted form, suspended in 10–90% by weight of an oily component, and comprising 1–50% by weight of a surfactant component, calculated on the total composition. This document does not teach how to include co-herbicides. Further it requires the glyphosate herbicide to be in a finely ground form, which is an expensive way of using glyphosate herbicide. The formulation disclosed also requires the presence of stabilizing agents.

European Patent Application 0 297 305 relates to aqueous herbicidal dispersions in combination with water-soluble plant protecting agents, comprising at least two actives in disperse form, at least one water-soluble herbicidally active ingredient and an appropriate surfactant mixture. Diphenyl ether type herbicides, e.g. oxyfluorfen, are cited as examples of dispersible material and glyphosate herbicide is cited as an example of water soluble material. The specified surfactant mixture is said to apply equally well for compositions comprising only one active material in dispersed form and one active material in soluble form. In the examples, the glyphosate loading is only 6–8% by weight. Furthermore, the dispersed form of active materials does not represent the most efficient form for application to plants, particularly in the case of systemic pesticides.

PCT Patent Application WO 91/14365 discloses that the systemic activity of glyphosate and other sprayed foliar systemic compositions may be improved by dissolving a substantially water soluble polymer in the spray solution. The polymer is generally introduced as a reverse phase dispersion. This document does not teach how to combine in an efficient manner glyphosate herbicide and a co-herbicide.

German Patent 40 13 930 discloses in its example 4, a concentrate composition that comprises glyphosate and acifluorfen which is a diphenyl ether herbicide, surfactant, polypropylene glycol and water. Such document discloses a liquid suspension of glyphosate comprising a rather low glyphosate loading, part of it being in a form insoluble in the medium of the composition and requiring milling. It is generally not desirable to formulate a water soluble herbicide as a suspension.

European patent application 0 334 041 discloses herbicidal compositions comprising a specific diphenylether herbicide and glyphosate. Formulation Example 1 of such prior art reference discloses an emulsifiable concentrate composition that comprises specific surfactants such as polyoyethylene styrylphenyl ether and sodium alkylbenzenesulfonate.

British patent application 2 267 825 has been filed prior to the priority date of the present patent application but published thereafter. It discloses herbicide microemulsion concentrate compositions comprising fluroypyr or triclopyr, which are water-insoluble herbicides, combined with a water soluble salt of glyphosate, together with at least one amine ethoxylate surfactant containing 2 to 5 moles of ethylene oxide, at least one amine ethoxylate surfactant containing 8 to 20 moles of ethylene oxide, and at least one cosurfactant.

There is still a need to provide a commercially acceptable liquid concentrated composition of this microemulsion or micellar solution type comprising N-phosphonomethylglycine or a salt thereof and at least one co-herbicide of the diphenyl ether type. The composition should be stable on storage, according to standards applicable to stable liquid formulations.

OBJECTS OF THE INVENTION

One object of the present invention is to provide a liquid transparent concentrated composition of the microemulsion type or micellar solution type comprising a glyphosate herbicide and a diphenyl ether type co-herbicide, having a high content of glyphosate-type herbicide, more specifically a content higher than about 15% by weight and preferably more than 20% by weight of acid equivalent based on the total composition.

Another object of the present invention is to provide a liquid concentrated composition as defined above that does not contain a high level of organic solvent, more especially one having a solvent content less than 10% by weight of the total composition.

Still another object of the present invention is to provide a cost-effective composition of glyphosate herbicide and at least one co-herbicide of the diphenyl ether type which shows a very good biological performance.

Another object of the present invention is to provide a liquid concentrated composition comprising N-phosphonomethylglycine or a salt thereof and at least one co-herbicide of the diphenyl ether type that does not show the drawbacks of the prior art herbicidal glyphosate compositions.

Still another object of the present invention is to provide a simple process for the preparation of a composition of the invention.

These and other objects of the invention are met in this invention as described more particularly below.

DETAILED DESCRIPTION OF THE INVENTION

According to the present invention, the liquid concentrate herbicidal composition of this invention comprises at least about 15% by weight based on the total composition of N-phosphonomethylglycine or of a salt thereof or of a mixture of salts thereof (calculated on a acid equivalent basis);

a water-insoluble diphenyl ether type herbicide in the ratio by weight of N-phosphonomethylglycine acid equivalent to diphenyl ether of from about 10:1 to about 100:1; and preferably from about 18:1 to about 72:1;

about 5 to about 25% by weight of a surface active component comprising a mixture of an alkoxylated fatty amine with a surfactant chemically different from the alkoxylated fatty amine:

about 0 to about 10% by weight (of total composition) of solvent; the surface active component optionally in admixture with the solvent being capable of dissolving the diphenyl ether herbicide;

about 1 to about 25% by weight of a compatibility agent; and water if necessary to total 100%.

The term "diphenyl ether type" herbicides includes diphenyl ether herbicides, their equivalents, metabolites, salts, esters and derivatives. Diphenyl ether herbicides are known by the skilled person and include compounds that have two generally substituted phenyl rings linked by an oxygen atom. Diphenyl ethers are commonly used in pre- and post-emergent application to crops to control annual broadleaf weeds and a few types of annual grasses.

They have been classified into two groups, primarily based on distinct differences in ring substitution and light requirement for herbicidal activity: one group with substitutions at the 2,4- or the 2,4,6- positions, the other group with substitutions at the 3- or 3,5- positions on one of the phenyl rings. Known herbicides pertaining to the group of diphenyl ethers are: nitrofen, aclonifen, acifluorfen, acifluorfen-sodium, acifluorfen-potassium, lactofen, fluorodifen, bifenox, chlomethoxyfen, oxyfluorfen, fluoroglycofen, fluoroglycofen-ethyl, fomesafen, 5-[ 2 -chloro-4-(trifluoromethyl)phenoxy]-2-nitroacetophenone oxime-o-(acetic acid, methyl ester) also known as DPE I, and 5-(2-chloro-4-trifluoromethylphenoxy)-2-nitro-α-methoxyacetophenone oxime-o-(acetic acid, methyl ester) also known as AKH-7088, mixtures thereof and the like.

In the context of the present invention, the term "solvent" includes any organic solvent or mixture thereof which does not have substantial surface active properties, and which would typically not be characterized as a surfactant by one skilled in the art. Suitable solvents may easily be selected by the skilled person amongst commercially available solvents. A good reference for selecting solvents is the "Industrial Solvents Handbook" Second Edition, by Ibert Mellan, Noyes Data Company, which is helpful when selecting a new solvent on a competitive or comparative basis, especially when the solvent employed hitherto may not be as desirable as formerly for environmental or other reasons. Solvents may be selected from hydrocarbon solvents, such as paraffins, cycloparaffins, olefins, cycloolefins, aromatics or terpenes, halogenated hydrocarbons, nitroparaffins, organic sulfur compounds, aldehydes, ethers, ketones, acids, amines including alkylamines, alkylene diamines, alkanol amines or aryl amines, imines, amides, nitriles and heterocyclic compounds, esters including formates, acetates, propionates, acrylates or methacrylates, oxalates, benzoates, carbonates, phthalates, phosphates or phosphites, oxygenated hydrocarbons and silicates, mixtures thereof and the like.

Preferred compatibility agents include monohydric alcohols including isopropanol, polyhydric alcohols, glycols and polyglycols including diethylene glycol (DEG), dipropylene glycol (DPG), monopropylene glycol (MPG) or low molecular weight (up to 500) polypropylene glycols (PPG), mixtures thereof and the like. Glycol ethers, such as 1-methoxy-2-propanol and dipropylene glycol monoether are also preferred. Butoxyethoxyethenol, such as 2-(2-n-butoxyethoxy)-ethenol, also known as butyl carbitol, is also considered as a compatibility agent according to the spirit of the present disclosure.

The microemulsion or micellar solution according to the present invention optionally contains water. Part of the water content may be due to the presence of water in commercial surfactants or surfactant mixtures and to the solution of glyphosate salt; additional water may be required in order to form the microemulsion or micellar solution.

In a preferred embodiment, the composition of the invention comprises at least 20% by weight (of total composition) of N-phosphonomethylglycine or of a salt thereof or of a mixture of salts thereof (calculated as acid equivalent). A preferred salt is the isopropylamine salt of glyphosate or normal propylamine salt of glyphosate. Other preferred salts are the ammonium salt or sodium salt of glyphosate or mixtures thereof.

As mentioned previously the ratio of glyphosate acid equivalent to diphenyl ether is of from about 10:1 to about 100:1; in a preferred composition said ratio is about 8:1; in another preferred embodiment, it is about 48:1 or about 72:1.

A suitable surface active component comprises one or more individual surface active materials. Suitable surface active materials may be selected amongst commercially available agriculturally acceptable surfactants. A good reference for selecting surfactants is "McCutcheon's Detergents and Emulsifiers Annual", MC Publishing Corp, Ridgewood, N.J. or equivalent technical documents. It is to be noted that commercial surfactants may comprise one or more individual surface active materials and possibly some water or solvent. The conditions the surfactant or the surfactant mix (surface active component) must fulfill is that the diphenyl ether herbicide dissolves in the surface active component optionally in admixture with the solvent and that such a solution is stable during a sufficient period of time to impart the required stability property to the final formulation according to conventional standards.

Suitable surface active materials other than the alkoxylated amine surfactant may include but are not limited to alkyl benzene sulfonates and alkyl naphthalene sulfonates, sulfated fatty alcohols, amines or acid amides, amine oxides, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the monohigher fatty acid esters of hexitol anhydrides (e.g. sorbitan), alkoxylated quaternary ammonium surfactants, alkylpolyglycosides, alkoxylated alcohol surfactants, alkoxylated fatty acid esters, sucrose esters possibly alkoxylated, silicone-based surfactants, mixtures thereof and the like.

In a preferred embodiment, the surfactant component is a mixture of an alkoxylated fatty amine and of an optionally alkoxylated quaternary ammonium salt. A suitable quaternary ammonium salt surfactant is alkyl dimethyl benzyl ammonium chloride, such as the commercial surfactant known as Dodigen 226 (tradename).

The composition of the present invention is a substantially clear or translucent liquid concentrate which does not present the properties of a traditional opaque emulsion.

The liquid composition of the present invention may be prepared by a process comprising the steps of:

(a) preparing a solution of a diphenyl ether type herbicide in a surface active component at a temperature in the range of from about 20° C. to about 80° C.;

(b) adding a solvent and optionally at least part of a compatibility agent and homogenizing the resulting solution;

(c) adding N-phosphonomethylglycine or a salt thereof, optionally in aqueous solution; and (d) adding the rest of the selected compatibility agent, such as by agitating the resulting mixture and if appropriate allowing it to cool;

or alternatively (a) preparing a solution of the diphenyl ether type herbicide in the surface active component at a temperature in the range of from about 20° C. to about 80° C.;

(b) adding at least part of a compatibility agent and homogenizing the resulting mixture;

(c) adding N-phosphonomethylglycine or a salt thereof, optionally in aqueous solution; and (d) optionally adding the rest of the compatibility agent by agitating the resulting mixture and if appropriate allowing it to cool;

or alternatively (a) preparing a solution of the diphenyl ether type herbicide in the solvent or in a mixture of solvent and at least part of a surface active component, at approximately ambient temperature;

(b) optionally adding a surface active component or part thereof, as appropriate, and at least part of a compatibility agent and homogenizing the resulting mixture;

(c) adding N-phosphonomethylglycine or a salt thereof, optionally in aqueous solution; and (d) optionally adding the rest of the compatibility agent by agitating the resulting mixture.

The solution of diphenyl ether type herbicide is preferably prepared by mixing the surfactant(s) with molten diphenyl ether type herbicide or stirring the diphenyl ether type herbicide in the surfactant mixture, optionally at elevated temperature. In the alternative, the solution may be prepared by admixing solvent, optionally the surfactant component or part thereof, and the diphenyl ether type herbicide at ambient temperature.

The glyphosate herbicide may be incorporated into the formulated product as the glyphosate acid or as a salt thereof, preferably the isopropylamine salt, or as a mixture of different salts. One may also combine glyphosate in its acid form with a suitable acid acceptor known in the art, such as ammonia, ammonium acetate, ammonium carbonate, ammonium bicarbonate, sodium acetate, potassium acetate, sodium bicarbonate, sodium carbonate, sodium metaborate, sodium citrate, tetrasodium EDTA, sodium formate, sodium hydroxide, sodium oxalate, trisodium phosphate, tripotassium phosphate, sodium propionate, sodium pyrophosphate, sodium metasilicate, sodium orthosilicate, sodium sulfite, sodium thiosulfate, sodium tetraborate, dipotassium phosphate, diammonium phosphate, sodium tripolyphosphate, sodium metaphosphate, ammonium and potassium salts thereof, mixtures thereof and the like but more preferably the acid acceptor is selected from ammonium bicarbonate, sodium bicarbonate, diammonium phosphate, disodium phosphate and mixtures thereof. The acid and the acid acceptor may be allowed to react in situ thus providing the required thermic energy for the preparation of the diphenyl ether type herbicide solution in surfactant.

According to another aspect of the present invention, a method of use of the liquid composition described above is provided. The exact amount of such composition containing N-phosphonomethylglycine and diphenyl ether type herbicide as the active ingredients to be employed is dependent upon the response desired in the plant, as well as such other factors as the plant species and stage of development thereof, the amount of rainfall, as well as the specific composition employed. In foliar treatment for the control of vegetative growth, the active ingredients are applied in amounts from about 0.01 to about 20 or more pounds per acre. An effective amount for phytotoxic or herbicidal control is that amount necessary for overall or selective control, i.e. a phytotoxic or herbicidal amount. It is believed that one skilled in the art can readily determine from the teachings of this specification the approximate application rate. The liquid formulation has first to be diluted in a water tank at the appropriate concentration, and the spray dilution may then be sprayed at the appropriate rate on the plants to be treated.

A liquid formulation of this invention, where the diphenyl ether type of co-herbicide is in a surfactant solution, typically forms a clear or translucent solution when diluted with water in a spray tank. Whilst the diphenyl ether type herbicide, e.g. fluoroglycofen ethyl, is sold as a water dispersible fine powder, the composition of the present invention allows a finer particle size for the fluoroglycofen ethyl active ingredient in the spray dilution. While it was previously taught (e.g. EP 0 503 869 cited previously) that oxyfluorfen, for instance, had to be milled before incorporation into an appropriate formulation, the present invention provides a liquid formulation comprising oxyfluorfen in a dissolved form, thus in the finest particle size suitable for a contact herbicide.

The following examples are presented to illustrate the present invention, as well as some of the various embodiments of the invention. These examples are presented as being illustrative of the novel formulations, process for preparing the formulations and herbicidal use thereof without any intention of limiting this invention in any way. All percentages in the following examples are on a weight basis unless otherwise indicated.

EXAMPLES

Example 1

A mixture of 50 parts Genamin C-020 (an ethoxylated (2EO) cocoamine surfactant) and 50 parts Prapagen WKT (a ditallow dimethyl ammonium chloride surfactant) was used to prepare a surfactant mix used in this and several following examples.

A solution of 1.85 parts by weight of oxyfluorfen (minimum 95% technical material from Rohm & Haas Company) in 12 parts of the surfactant mix described above was prepared at approximately 50° C. Thereafter, 8.15 parts of cyclohexanone were added and the solution was homogenized. Then 67 parts of a 62% solution of glyphosate isopropylamine salt were incorporated into the solution and the compatibility agent (11 parts of dipropylene glycol) was added under agitation. The mixture was allowed to cool at room temperature. The liquid concentrate composition thereby formed was stable at least above 5° C.

Example 2

The same procedure as described in Example 1 was followed, but in this Example 2 the solvent content was reduced. A satisfactorily stable liquid composition was obtained having the following ingredients:

| | | |
|---|---|---|
| IPA salt of glyphosate (62% solution) | 67.00 | (30.74 a.e.) |
| Oxyfluorfen (min. 95% active ingredient | 1.85 | |
| Surfactant mix of Example 1 | 15.50 | |
| Cyclohexanone (solvent) | 7.65 | |
| DPG* (compatibility agent) | 8.00 | |
| Total | 100.00 | |

*dipropylene glycol

Example 3

The solvent content was further reduced. A satisfactorily stable liquid composition having the following ingredients was obtained:

| | | |
|---|---|---|
| IPA salt of glyphosate (62% solution) | 67.00 | (30.74 a.e.) |
| Oxyfluoren (min. 95% active ingredient) | 1.85 | |
| Surfactant mix of Example 1 | 15.50 | |
| Cyclohexanone | 5.65 | |
| DPG | 10.00 | |
| Total | 100.00 | |

Examples 4 and 5

Substantially the same procedure as in the previous Examples 1–3 was followed except as noted below. Satisfactorily stable liquid compositions having the following ingredients were obtained:

| | | |
|---|---:|---|
| IPA salt of glyphosate (62% solution) | 67.00 | (30.74 a.e.) |
| Oxyfluorfen (min. 95% active ingredient) | 1.85 | |
| Surfactant mix of Example 1 | 24.20 | |
| Cyclohexanone | 6.95 | |
| DPG | — | |
| Total | 100.00 | |

| | | |
|---|---:|---|
| IPA salt of glyphosate (62% solution) | 67.00 | (30.74 a.e.) |
| Oxyfluorfen (min. 95% active ingredient) | 1.85 | |
| Surfactant mix of Example 1 | 19.20 | |
| Cyclohexanone | 7.00 | |
| DEG* | 4.95 | |
| Total | 100.00 | |

*diethylene glycol

Example 6

In this instance, another surfactant mix was used, comprising Genamin C-020, an ethoxylated (2EO) cocoamine surfactant, and Empigen OB, an amine oxide surfactant.

The following liquid concentrate composition was stable:

| | | |
|---|---:|---|
| IPA salt of glyphosate (62% solution) | 60.00 | (27.53 a.e.) |
| Oxyfluorfen (min. 95% active ingredient) | 1.70 | |
| Genamin C-020 | 5.50 | |
| Empigen OB | 10.00 | |
| Cyclohexanone | 7.89 | |
| DPG | 15.00 | |
| Total | 100.00 | |

Example 7

The following liquid concentrate composition was obtained following essentially the procedure of the previous Examples 1–6 except that no solvent, in the sense of the invention, was used.

| | | |
|---|---:|---|
| IPA salt of glyphosate (62% solution) | 59.00 | (27.07 a.e.) |
| Oxyfluorfen (min. 95% active ingredient) | 1.55 | |
| Genamin C-020 | 12.00 | |
| Prapagen WKT | 3.20 | |
| DPG | 15.00 | |
| Water | 9.25 | |
| Total | 100.00 | |

Example 8

The following stable liquid concentrate composition was obtained following closely the procedure of the previous Examples 1–7. In this Example 8, the surfactant mix comprised Genamin C-020 surfactant and Dodigen 226 (cocoalkyldimethylbenzyl ammonium chloride):

| | | |
|---|---:|---|
| IPA salt of glyphosate (62% solution) | 67.00 | (30.74 a.e.) |
| Oxyfluorfen (min. 95% active ingredient) | 1.85 | |
| Genamin C-020 | 7.70 | |
| Dodigen 226 | 7.70 | |
| Cyclohexanone | 5.75 | |
| DPG | 10.00 | |
| Total | 100.00 | |

Example 9

The following stable concentrate composition was obtained following essentially the same procedure as previously described:

| | | |
|---|---:|---|
| IPA salt of glyphosate (62% solution) | 55.60 | (25.50 a.e.) |
| Oxyfluorfen (min. 95% active ingredient) | 1.40 | |
| Genamin T-200 NF* | 10.00 | |
| Empigen OB | 18.00 | |
| Cyclohexanone | 5.00 | |
| DPG | 10.00 | |
| Total | 100.00 | |

*Genamin T-200 NF contains an ethoxylated (15EO) tallowamine surfactant.

Example 10

A mixture of 50 parts of Genamin C-020 and 50 parts Prapagen WKT was prepared to constitute a surfactant mix.

A solution of 2 parts of fluoroglycofen-ethyl (approximately 88% technical material) in 15 parts of the surfactant mix described above was prepared at approximately 65° C. Some DPG compatibility agent may be added at this point, homogenizing the mixture. Then 67 parts of a 62% solution of glyphosate isopropylamine salt were incorporated into the solution and the residual compatibility agent (16 parts of DPG in total) was added under agitation. The mixture was allowed to cool at room temperature.

The resulting liquid concentrate composition was stable.

Example 11

A solution of 2 parts of fluoroglycofen ethyl (approx. 88% technical material) in a mixture of 10 parts of Genamin C-020 and 7 parts of Dodigen 226 was prepared at a temperature of about 65° C. Thereafter, 6 parts of cyclohexanone were added under agitation and 67 parts of a 62% solution of glyphosate isopropylamine salt were incorporated into the solution. Then 8 parts of DPG were added and the mixture was allowed to cool. The composition was stable at normal temperatures.

Example 12

The same procedure as in Example 1 was followed and the stable liquid concentrate formulation having the following composition was obtained:

| | | |
|---|---:|---|
| IPA salt of glyphosate (62% solution) | 67.00 | (30.74 a.e.) |
| Oxyfluorfen (min. 95% active ingredient) | 1.85 | |

| | |
|---|---|
| surfactant mix of Example 1 | 12.00 |
| Solvesso 150* | 8.15 |
| DPG | 11.00 |
| Total | 100.00 |

*aromatic hydrocarbon solvent from Exxon Chemicals, having more than 99% by weight aromatic content.

Example 13

Following the same procedure as in Example 1 a liquid stable concentrate composition was obtained, having the following composition:

| | | |
|---|---|---|
| IPA salt of glyphosate (62% solution) | 67.00 | (30.74 a.e.) |
| Oxyfluorfen (min. 95% active material) | 1.85 | |
| Surfactant mix of example 1 | 12.00 | |
| Exxate 600* | 8.15 | |
| DPG | 11.00 | |
| Total | 100.00 | |

*oxygenated hydrocarbon solvent from Exxon Chemicals.

Example 14

Following the same procedure as in Example 1, a liquid stable concentrate composition was obtained, having the following composition:

| | | |
|---|---|---|
| IPA salt of glyphosate (62% solution) | 40.52 | (18.84 a.e.) |
| Oxyfluorfen (min. 95% active ingredient) | 0.99 | |
| Genamin C-020 | 6.09 | |
| Empigen OB | 28.03 | |
| Cyclohexanone | 6.09 | |
| DPG | 18.28 | |
| Total | 100.00 | |

Example 15

Following essentially the procedure of Example 1, 1.85 parts of acifluorfen (81.4% technical material from Rohm & Haas) were heated at approximately 50° C. and dissolved in 12 parts of the surfactant mix prepared in Example 1. Thereafter 8.15 parts of cyclohexanone were added and the solution was stirred. Then 67 parts of a 62% solution of glyphosate isopropylamine salt were incorporated into the solution and the compatibility agent (11 parts of DPG) was added under agitation. The mixture was allowed to cool at room temperature and a stable liquid concentrate composition was obtained.

Example 16

Another formulated composition according to the present invention has the following composition of materials:

| | | |
|---|---|---|
| IPA salt of glyphosate (62% solution) | 47.0 | (22.8 a.e.) |
| Oxyfluorfen (70% active ingredient) | 1.5 | |
| Cyclohexanone | 4.0 | |
| N-methylpyrrolidone | 3.0 | |
| bis(polyoxyethylene)alkyl methyl ammonium chloride | 7.2 | |
| bis(polyoxyethylene) alkylamine | 1.2 | |
| polyoxyethylene alkyl phenyl ether | 1.2 | |
| propylene glycol | 2.4 | |
| diethylene glycol monobutyl ether | 18.0 | |
| water | 14.5 | |
| Total | 100.0 | |

Example 17

Three other compositions were prepared according to the present invention.

| | % w/w | % w/w | % w/w |
|---|---|---|---|
| IPA salt of glyphosate (62%) | 67.00 | 67.00 | 67.00 |
| oxyfluorfen, 95% | 1.85 | 0.67 | 0.45 |
| Genamin C-020 | 6.50 | 6.50 | 6.50 |
| Dodigen 226 | 4.50 | 4.50 | 4.50 |
| Cyclohexanone solvent | 7.50 | 7.50 | 7.50 |
| Butyl Carbitol | 7.50 | 7.50 | 7.50 |
| DPG | 5.15 | 6.33 | 6.55 |
| | 100.00 | 100.00 | 100.00 |

What is claimed

1. A stable aqueous-based liquid concentrate herbicidal composition having a separate phase in the form of a microemulsion or micellar solution comprising:
   a) at least 15% of a water soluble herbicidal salt of N-phosphonomethylglycine a.e. dissolved in said liquid;
   b) a water-insoluble diphenylether herbicide selected from the group consisting of oxyfluorfen and acifluorfen dissolved in an inert organic solvent and suspended in the aqueous liquid, the ratio by weight of N-phosphonomethylglycine herbicide a.e. to the diphenylether herbicide being from abut 10:1 to about 100:1;
   c) about 5 to about 25% by weight of a surfactant mixture of (i) an alkoxylated fatty amine surfactant and (ii) an alkoxylated quaternary ammonium salt surfactant;
   d) about 1 to about 25% by weight of a compatibility agent selected from the group consisting of dipropylene glycol and diethylene glycol; and
   e) the remainder water.

2. The composition of claim 1 wherein at least 20% by weight is a herbicidal salt of glyphosate.

3. The composition of claim 2 wherein the herbicidal salt is the isopropylamine salt of N-phosphonomethylglycine.

4. The composition of claim 3 wherein the diphenylether herbicide is oxyfluorfen.

5. The composition of claim 3 wherein the diphenylether herbicide is acifluorfen.

6. The composition of claim 3 wherein the compatibility agent is dipropylene glycol.

7. The composition of claim 3 wherein the compatibility agent is diethylene glycol.

8. The composition of claim 3 wherein the solvent is cyclohexanone.

9. The composition of claim 3 wherein the alkoxylated fatty amine surfactant is ethoxylated (2EO) cocoamine.

10. The composition of claim 3 wherein the quaternary ammonium salt surfactant is cocoalkyldimethylbenzyl ammonium chloride.

11. A method of killing or controlling unwanted vegetation by applying to the plants to be killed or controlled an effective amount of the composition of claim 1.

* * * * *